(12) United States Patent
Harzig et al.

(10) Patent No.: US 10,910,100 B2
(45) Date of Patent: Feb. 2, 2021

(54) SYSTEM AND METHOD FOR GENERATING DESCRIPTIONS OF ABNORMALITIES IN MEDICAL IMAGES

(71) Applicant: FUJI XEROX CO., LTD., Tokyo (JP)

(72) Inventors: Philipp Daniel Harzig, Bavaria (DE); Yin-Ying Chen, San Jose, CA (US); Francine Chen, Menlo Park, CA (US)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 16/354,003

(22) Filed: Mar. 14, 2019

(65) Prior Publication Data
US 2020/0294654 A1 Sep. 17, 2020

(51) Int. Cl.
| | |
|---|---|
| *G06F 17/00* | (2019.01) |
| *G16H 30/40* | (2018.01) |
| *G06K 9/46* | (2006.01) |
| *G06T 7/00* | (2017.01) |
| *G16H 15/00* | (2018.01) |
| *G16H 50/20* | (2018.01) |
| *G06F 40/30* | (2020.01) |
| *G06F 40/279* | (2020.01) |

(52) U.S. Cl.
CPC .......... *G16H 30/40* (2018.01); *G06F 40/279* (2020.01); *G06F 40/30* (2020.01); *G06K 9/4604* (2013.01); *G06T 7/0012* (2013.01); *G16H 15/00* (2018.01); *G16H 50/20* (2018.01); *G06T 2207/20081* (2013.01)

(58) Field of Classification Search
CPC ........ G16H 30/40; G16H 15/00; G16H 50/20; G06F 40/279; G06F 40/30; G06K 9/4604; G06T 7/0012

USPC ......................................................... 715/231
See application file for complete search history.

(56) References Cited

U.S. PATENT DOCUMENTS

| | | | | |
|---|---|---|---|---|
| 10,140,421 | B1 * | 11/2018 | Bernard | ................ G06T 7/0016 |
| 10,755,413 | B1 * | 8/2020 | Putha | ........................ G06T 7/11 |
| 2002/0190980 | A1 * | 12/2002 | Gerritsen | ................ G06T 19/00 |
| | | | | 345/419 |
| 2004/0122707 | A1 * | 6/2004 | Sabol | ..................... G16H 50/20 |
| | | | | 705/2 |

(Continued)

OTHER PUBLICATIONS

Pimentel et al., A Review of Novelty Detection, Elsevier 2014, pp. 215-249. (Year: 2014).*

(Continued)

*Primary Examiner* — Cong-Lac Huynh
(74) *Attorney, Agent, or Firm* — Procopio, Cory, Hargreaves & Savitch LLP

(57) ABSTRACT

A method and system for determining a treatment order for a plurality of patient imaging records. The method includes extracting, by a trained neural network, image features from each of the plurality of imaging records, generating, by the trained neural network, a written report associated with each of the plurality of imaging records based on the extracted image features, wherein the trained neural network generates the written report based on a sentence annotation model that provides abnormality annotations on an individual sentence basis, determining, by the trained neural network, an abnormality score associated with each written report, and providing the written reports to a treating physician in a sorted order based on the abnormality score associated with each written report.

20 Claims, 7 Drawing Sheets

(56) References Cited

U.S. PATENT DOCUMENTS

| | | | | |
|---|---|---|---|---|
| 2004/0122787 | A1* | 6/2004 | Avinash | G16H 50/20 706/50 |
| 2006/0274928 | A1* | 12/2006 | Collins | A61B 8/00 382/132 |
| 2015/0073958 | A1* | 3/2015 | Schweer | G06Q 40/00 705/35 |
| 2017/0262584 | A1* | 9/2017 | Gallix | G06N 20/00 |
| 2018/0033023 | A1* | 2/2018 | Pereira | G06Q 30/0201 |
| 2019/0005686 | A1* | 1/2019 | Liu | G06T 11/008 |
| 2019/0041078 | A1* | 2/2019 | Harpale | G06N 3/08 |
| 2019/0183366 | A1* | 6/2019 | Dehghan Marvast | G06T 7/0012 |
| 2019/0340763 | A1* | 11/2019 | Laserson | G06T 7/0012 |
| 2020/0043600 | A1* | 2/2020 | Glottmann | G06F 40/154 |
| 2020/0151871 | A1* | 5/2020 | Putha | G06N 3/08 |
| 2020/0160973 | A1* | 5/2020 | Andersen | G16H 30/40 |

OTHER PUBLICATIONS

Vinyals, O. et al., "Show and Tell: A Neural Image Caption Generator" 2015 IEEE Conference on Computer Vision and Pattern Recognition, 2015, 9 pages.

Krause, J. et al., "A Hierarchical Approach for Generating Descriptive Image Paragraphs" 2017 IEEE Conference on Computer Vision and Pattern Recognition, 2017; 9 pages.

Wang, X. et al., "TieNet: Text-Image Embedding Network for Common Thorax Disease Classification and Reporting in Chest X-rays" 2018 IEEE Conference on Computer Vision and Pattern Recognition, 2018; 10 pages.

Jing, B. et al. "On the Automatic Generation of Medical Imaging Reports" Proceedings of the 56th Annual Meeting of the Association for Computational Linguistics, Jul. 15-20, 2018; 10 pages, Melbourne, Australia.

Kohli, R. "Indiana University Chest X-ray Collection" https://openi.nlm.nih.gov/detailedresult?img=CXR1261_IM-0177-1001&query=Mild%20cardiomegaly.%20Normal%20pulmonary%20vascularity.&it=xg&req=4&npos=1; 2013 (Accessed Mar. 14, 2019); 1 page.

Wang, X. et al. "ChestX-ray8: Hospital-scale Chest X-ray Database and Benchmarks on Weakly-Supervised Classification and Localization of Common Thorax Diseases" 2017 IEEE Conference on Computer Vision and Pattern Recognition; 2017 (Accessed Mar. 14, 2019); 10 pages.

Kohli, R. "Indiana University Chest X-ray Collection" https://openi.nlm.nih.gov/detailedresult?img=CXR1900_IM-0584-2001&query=stable%20appearance%20of%20the%20chest.%20no%20acute%20process&it=xg&req=4&npos=2; 2013 (Accessed Mar. 14, 2019); 1 page.

* cited by examiner

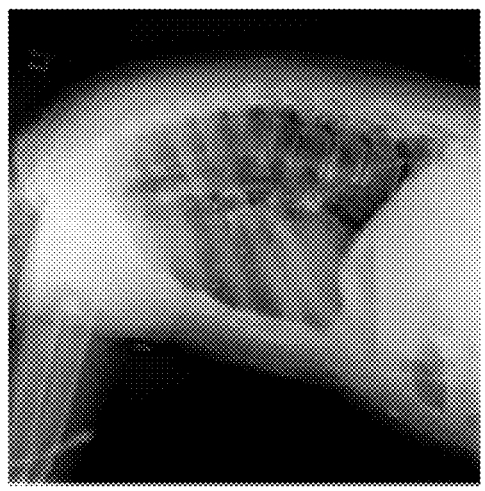

(a) w/o abnormal sentence annotation no acute osseous abnormality . the heart size and pulmonary vascularity appear within normal limits . the lungs are clear . the lungs are clear . the skeletal structures are normal .

(b) with abnormal sentence annotation no evidence of acute cardiopulmonary process . the lungs are clear . the lungs are clear . there are mild degenerative changes of the spine .

(c) Groundtruth

Stable appearance of the chest. No acute process. There are XXXX sternotomy XXXX identified. The heart is within normal limits in size. The aorta is calcified and tortuous. There are scattered calcified granulomas throughout both lungs. No focal infiltrate, pleural effusion, or pneumothorax. Mild degenerative changes of the thoracic spine.

FIG. 5

SYSTEM AND METHOD FOR GENERATING DESCRIPTIONS OF ABNORMALITIES IN MEDICAL IMAGES

BACKGROUND

Field

The present disclosure relates to generation of text descriptions, and more specifically, to systems and methods for computer-aided generation of descriptions of abnormalities in new medical images.

Related Art

Writing reports for medical images, especially multi-sentence descriptions, using manual techniques may be time consuming and requires expert knowledge. With a limited workforce of medical professionals and their increasing workload, related art machine-assisted image report generation methods and systems have been developed recently. For example, related art approaches have exported generating multi-sentence descriptions for Chest X-ray images. However, these related art approaches have assumed all words in a description are equally important for optimizing a model. This does not appropriately apply to medical reports where certain sentences in a report may be worth more attention than others, particularly those regarding medical abnormality, and thus require higher accuracy.

SUMMARY OF THE DISCLOSURE

Aspects of the present application may include a method of determining a treatment order for a plurality of patent imaging records. The method may include extracting, by a trained neural network, image features from each of the plurality of imaging records, generating, by the trained neural network, a written report associated with each of the plurality of imaging records based on the extracted image features, wherein the trained neural network generates the written report based on a sentence annotation model that provides abnormality annotations on an individual sentence basis, determining, by the trained neural network, an abnormality score associated with each written report, and providing the written reports to a treating physician in a sorted order based on the abnormality score associated with each written report.

Additional aspects of the present application may include a non-transitory computer readable medium encoded with instructions for making a computing device execute a method of determining a treatment order for a plurality of patent imaging records. The method may include extracting, by a trained neural network, image features from each of the plurality of imaging records, generating, by the trained neural network, a written report associated with each of the plurality of imaging records based on the extracted image features, wherein the trained neural network generates the written report based on a sentence annotation model that provides abnormality annotations on an individual sentence basis, determining, by the trained neural network, an abnormality score associated with each written report, and providing the written reports to a treating physician in a sorted order based on the abnormality score associated with each written report.

Further aspects of the present application may include a computing device having a memory storage device storing a plurality of patient imaging records, and a processor communicatively coupled to the memory storage device. The processor may be configured to perform a method of determining a treatment order for a plurality of patent imaging records. The method may include extracting, by a trained neural network, image features from each of the plurality of imaging records, generating, by the trained neural network, a written report associated with each of the plurality of imaging records based on the extracted image features, wherein the trained neural network generates the written report based on a sentence annotation model that provides abnormality annotations on an individual sentence basis, determining, by the trained neural network, an abnormality score associated with each written report, and providing the written reports to a treating physician in a sorted order based on the abnormality score associated with each written report.

Further aspects of the present application may include a computing device including means for storing a plurality of patient imaging records, means for extracting, by a trained neural network, image features from each of the plurality of imaging records, means for generating, by the trained neural network, a written report associated with each of the plurality of imaging records based on the extracted image features, wherein the trained neural network generates the written report based on a sentence annotation model that provides abnormality annotations on an individual sentence basis, means for determining, by the trained neural network, an abnormality score associated with each written report, and means for providing the written reports to a treating physician in a sorted order based on the abnormality score associated with each written report.

BRIEF DESCRIPTION OF THE DRAWINGS

FIGS. 5 and 6 illustrate examples of a generated text reports for input X-ray images in accordance with example implementations of the present application.

DETAILED DESCRIPTION

Figure 1:
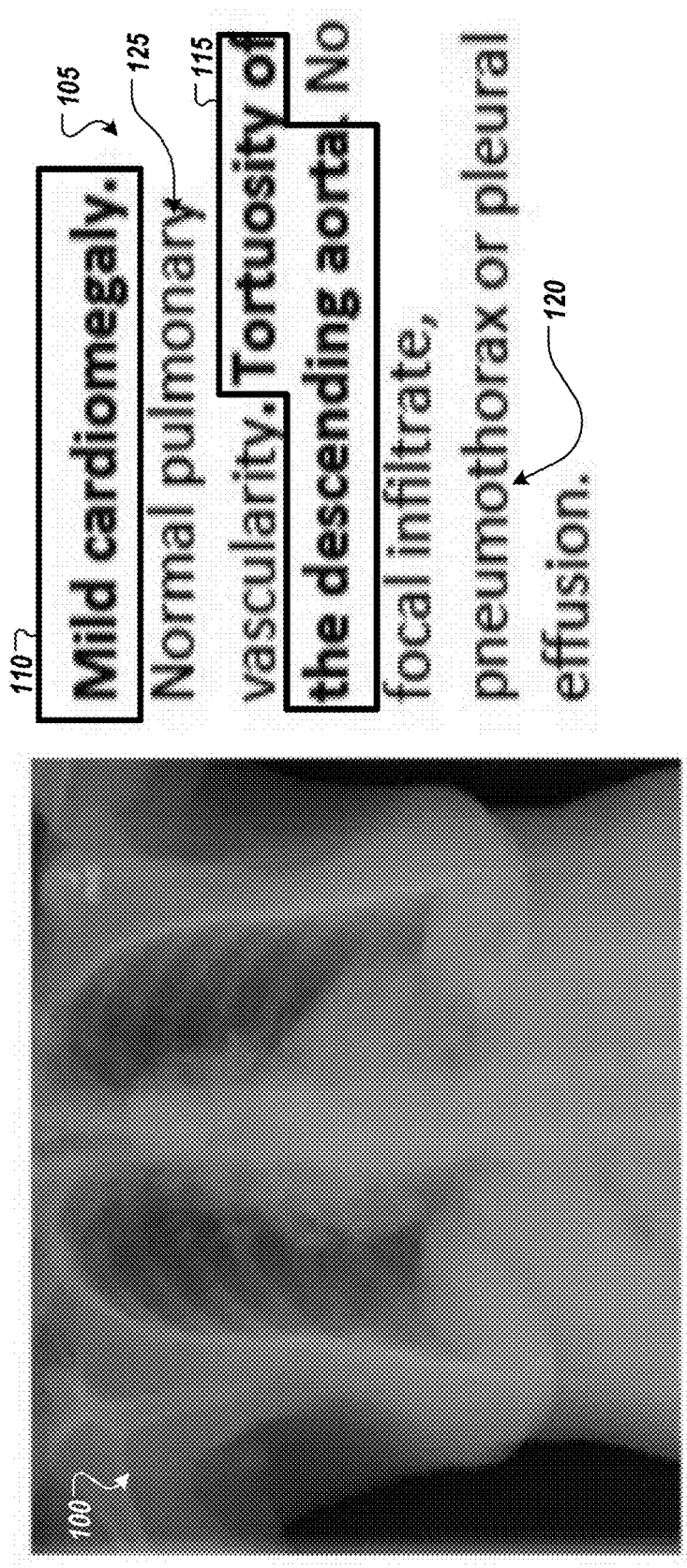
FIG. 1 illustrates a diagnostic medical image and an associated textual description as from which a medical report may be generated by example implementations of the present application.

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or operator control over certain aspects of the implementation, depending on the desired implementation of one of ordinary skill in the art practicing implementations of the present application. Further, sequential terminology, such as "first", "second", "third", etc., may be used in the description and claims simply for labeling purposes and should not be limited to referring to described actions or items occurring in the described sequence. Actions or items may be ordered into a different sequence or may be performed in parallel or dynamically, without departing from the scope of the present application.

In the present application, the terms computer readable medium may include a local storage device, a cloud-based storage device, a remotely located server, or any other storage device that may be apparent to a person of ordinary skill in the art.

As described above, typical image captioning tasks usually regard words in a description equally important for optimizing a model. This does not appropriately apply to medical reports where certain sentences in a report may be worth more attention than others, particularly those regarding medical abnormality, and require higher accuracy. To address this situation, the present application describes a system that may integrate knowledge of medical abnormalities at the sentence level for learning a report generation model. Additionally, at least two approaches to identifying sentences describing medical abnormalities are illustrated that may further reduce the burden of labeling training data.

The present application recognizes that improving turn-around time for preparing medical image reports may be an important topic in healthcare research and industry because timely diagnostic information can be critical for both patients and physicians. With an ever-growing line of patients, usage of machine-assisted diagnosis may alleviate the workload of medical professionals. However, the related art work in this area has focused on disease classification where the generated annotations are usually a compact medical term or a short-phrase tag. However, in some situations, a medical image report may include more details than tags that explain the diagnosis. For example, in some situations, medical report findings may include multi-sentence natural language descriptions of the biological structures shown in the image.

In order to generate multi-sentence descriptions, related art approaches for image captioning have been recently adopted to medical image report generation. However, medical image report generation is different from typical image captioning tasks because with typical image captioning tasks, the words in a description are generally equally important for optimizing a model. However, certain sentences in a medical report may be worth more attention than others. For example, descriptions of normal biological structures are often less important than descriptions of the medical abnormalities.

FIG. 1 illustrates a diagnostic medical image 100 and an associated textual description 105 as from which a medical report may be generated by example implementations of the present application.[1] As illustrated, the associated textual description 105 includes multiple clauses 110, 115, 120, and 125. However, two of these clauses describe normal biological structures 125 or the absence of potentially abnormal structures 120. Thus, of the four clauses 110, 115, 120, 125, only two clauses 110 and 115 describe abnormal structures, which are more diagnostically relevant then cause describing the normal biological structures 125 or the absence of potentially abnormal structures 120.

As a corpus of medical image reports collected for training of an automatic report generation system would include a significant volume of less diagnostically relevant descriptions (e.g. descriptions of normal biological structures such as clause 125 or statements noting the absence of abnormal structures such as clause 120). If such training data is used, optimizing loss over all words may not reflect the loss on the sentences or clauses about abnormalities, especially when the descriptions of the abnormalities are not a majority of the training data. In some related art projects have noted that with training data with "only a few sentences are about the abnormalities . . . it [a trained model] can just generate the normalities to easily obtain a high score."

[1] Medical image 100 was obtained from NIH Clinical Center Repository available at https://openi.nlm.gov/detaledresult?img=CXR1261_IM-0177-1001&query=Mild%20cardiornegaly.%20Normal%20pulmonary?20 vascularity.&it=xg&req=4&npos=1 and discussed in Wang X, Peng Y, Lu L, Lu Z, Bagheri M, Summers R M. ChestX-ray8: Hospital-scale Chest X-ray Database and Benchmarks on Weakly-Supervised Classification and Localization of Common Thorax Diseases. IEEE CVPR 2017, http://openaccess.thecvf.com/content_cvpr_2017/papers/Wang_ChestX-ray8_Hospital-Scale_Chest_CVPR_2017_paper.pdf In order to prevent a develop report generation model from learning to neglect abnormality descriptions, example implementations of the present application may integrate annotations of abnormal sentences into the developed model. These annotations may be used to explicitly or implicitly assign weighting factors for sentences of a report in the training data or assign sentences of a report in the training data to different language models. Further in some example implementations abnormality annotations may be labeled by a human or identified automatically. Within the example implementations described herein at least two approaches are illustrated to identify sentences relating to abnormalities to potentially labeling effort burden.

Further, in some example implementations the abnormality identification approaches may also be applied to a generated report in combined with the prediction score to provide suggestions of different practices of physician review depending on the confidence score. For example multiple reviewers of the diagnostic image may be assigned to reports indicating high degrees of abnormalities associated with low prediction confidence scores to reduce chances of false or inaccurate diagnosis.

Figure 2:
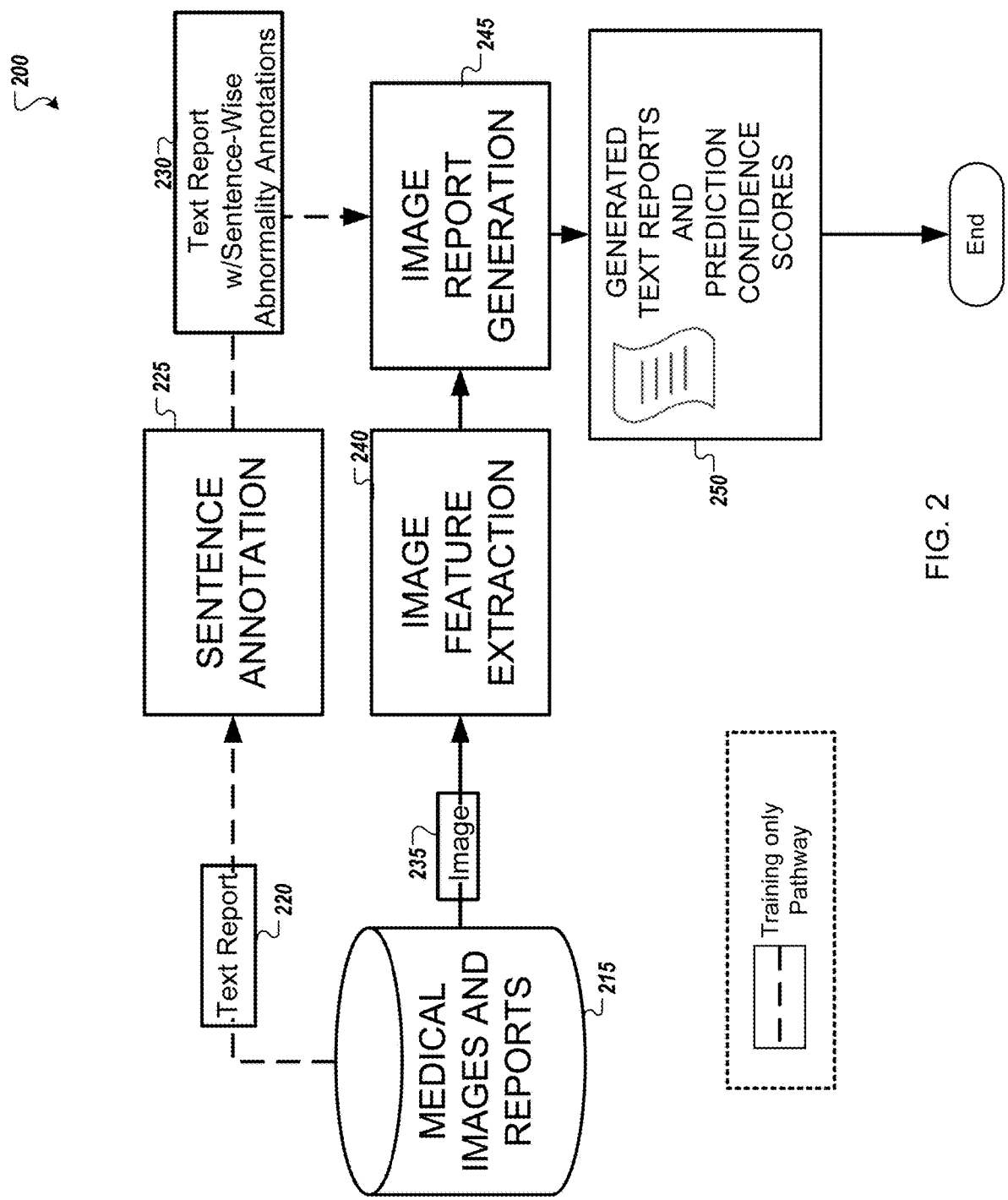
FIGS. 2 and 3 illustrate schematic representations of a medical report generation system in accordance with example implementations of the present application.
Figure 3:
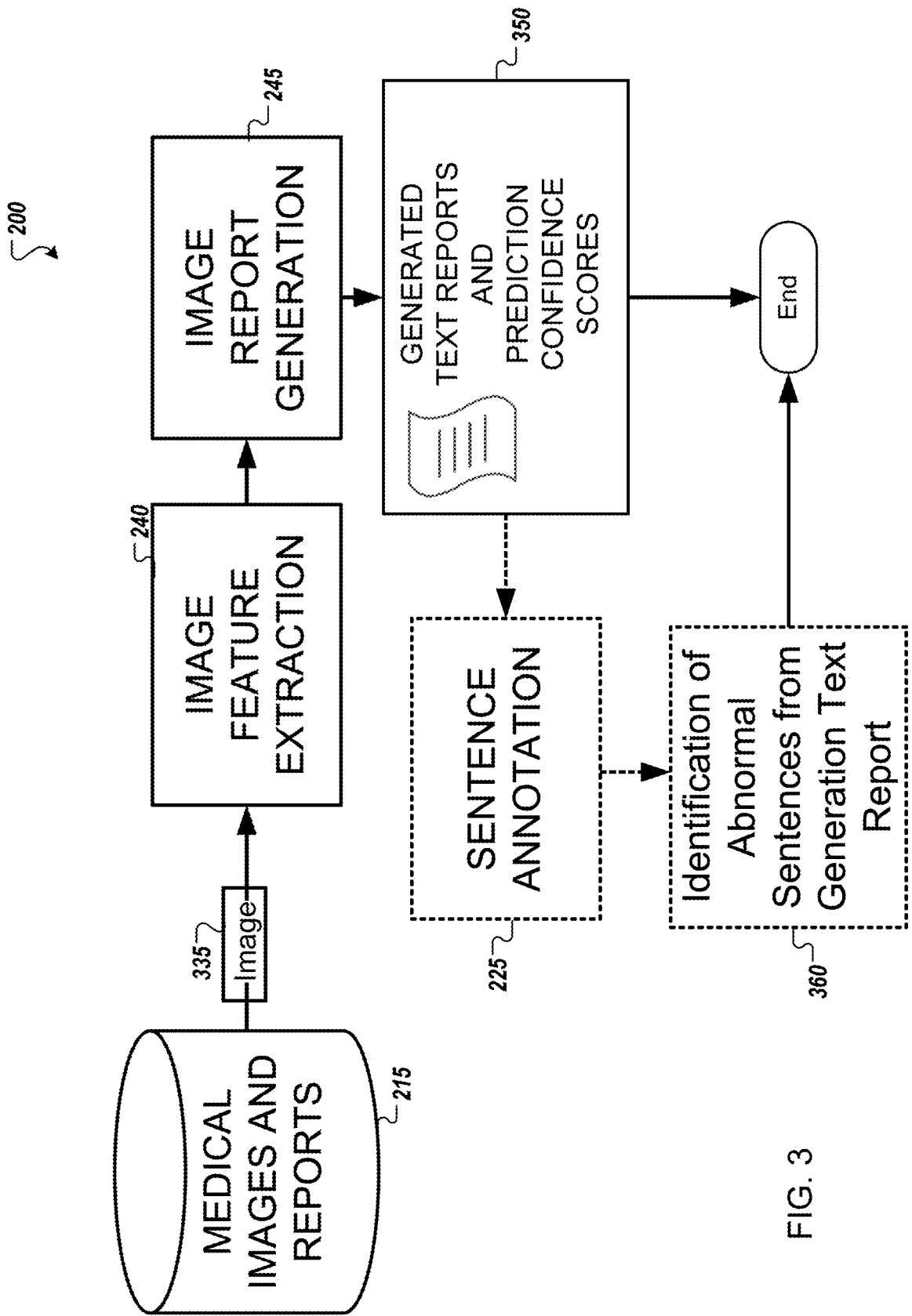

FIGS. 2 and 3 illustrate schematic representations of a medical report generation system 200 in accordance with example implementations of the present application. In FIG. 2, the system 200 is illustrated in a training phase and in FIG. 3, the system 200 is illustrated in a testing phase. As illustrated in FIG. 2, the training phase includes all of the actions performed during the testing phase plus additional actions performed only during the training phase. During the training phase, each image 235 in the training data of a corpus of medical images and reports 215, each image in the training data being associated with a text report 220 that include multi-sentence descriptions of each image 235. The corpus of medical images and reports 215 may include training data including both images and associated reports, and testing data including only images.

Further, during the training phase, the abnormal sentences in each text report 220 are identified and annotated by a human, and automatic annotation model using a neural network, or a combination of human action, a semi-automatic annotation model (e.g. an automated annotation model which provide suggestions for approval by a human) or a combination thereof at 225. The sentence annotation of 225 produces a text report incorporating sentence wise abnormality annotations 230.

By using a neural network to annotate the training data on a per sentence basis greater weight may be placed on the sentences representative of abnormalities as such sentences are often more diagnostically important as compared to sentences describing normal structures.

Alternatively, by using a neural network to annotate the training data on a per sentence basis, an appropriate language model may be assigned for a sentence based on its annotations. This may avoid sentences representative of abnormalities from being interfered by sentences describing normal structures.

In parallel during the training phase, the image 235 associated with the text report 220 is passed through an image feature extraction model 240 on a neural network to train the image feature extraction model 240 to extract feature representations of image content. The image feature extraction model 240 may use object recognition techniques to detect shapes, textures, or other aspects of biological structures in the medical image in order to recognize biological structures and distinguish normal structures from abnormal structures. The object recognition techniques used by the image feature extraction model 240 may be any object recognition techniques that might be apparent to person of ordinary skill in the art.

After the image feature extraction model 240 has extracted feature representations of image content of the image 235, a text generation model 245 on a neural network is trained to predict words in the sentences of text report 220 sequentially by considering the extracted feature representations of image content of the image 235 and previously predicted words of the text generation model 245 to generate text reports 250. During the training of the text generation model 245, optimization loss may be calculated according to the loss of word predictions and sentence annotations, where the annotations are determined based on how likely a sentence being generated is describing a medical abnormality based on the sentence wise abnormality annotations provided by the sentence annotation model 225.

In some example implementations, a hierarchical text generation model on a neural network may be used to generate the text report. For example, several topics may be generated, each topic to be presented by a sentence. Then each sentence may be generated word by word based on the sentence wise abnormality annotations. Once a text report 250 is generated for each image in the training data of the corpus 215, the training phase may end.

As illustrated in FIG. 3, during the testing phase, the system 200 may use the trained image feature extraction model 240 on the neural network to extract features of an input image 335 and may use the image report generation model 245 on the neural network to sequentially predict words to generate a text report 350. In some example implementations, prediction probabilities associated with each word in a generated sentence may be aggregated to provide a prediction confidence for an entire sentence. After a text report and confidence score is generated for each image 335 in the testing data of the corpus 215 of medical images and reports the testing phase may end.

In some example implementations, a hierarchical text generation model on a neural network may be used to generate the text report. For example, several topics may be generated, each topic to be presented by a sentences. Then each sentence may be generated word by word based on the sentence wise abnormality annotations, with the prediction confidence associated with each generated word being aggregated to provide prediction confidence for an entire sentence.

Further, in some example implementations, the generated text report 350 may be processed through the sentence annotation model 225 on the neural network used during the training phase to provide an identification 360 of abnormal sentences in each generated text report 350. By analyzing each sentence in the generated report to determine, a determination of which sentences relate to abnormalities may be made. Further, in some example implementations, an abnormality score representing the number of abnormality sentences in the report may be determined. This abnormality score may be used to automatically prioritize which reports relate to images with the most number of abnormalities and which reports relate to relative normal images. For example, a report with 5 abnormality related sentences may be prioritized over a report with on 1 abnormality sentence.

Thus, in some example implementations a system may allow large numbers of reports to be sorted and prioritized based on the number of abnormality related sentences are detected in the reports, saving doctor time and allowing doctors to more quickly respond to the most serious cases. For example, the system may provide or recommend a treatment order in, which the doctor should review medical images and treat patients based on a detected or projected severity of the patient diagnosis determined from the medical images. Thus, in some embodiments a system may provide a prioritized list of reports showing the most abnormalities to facilitate timely patient care.

In some example implementations, the testing phase may end after identification 360 of abnormal sentences in each generated text report 350.

Figures 4A, 4B:
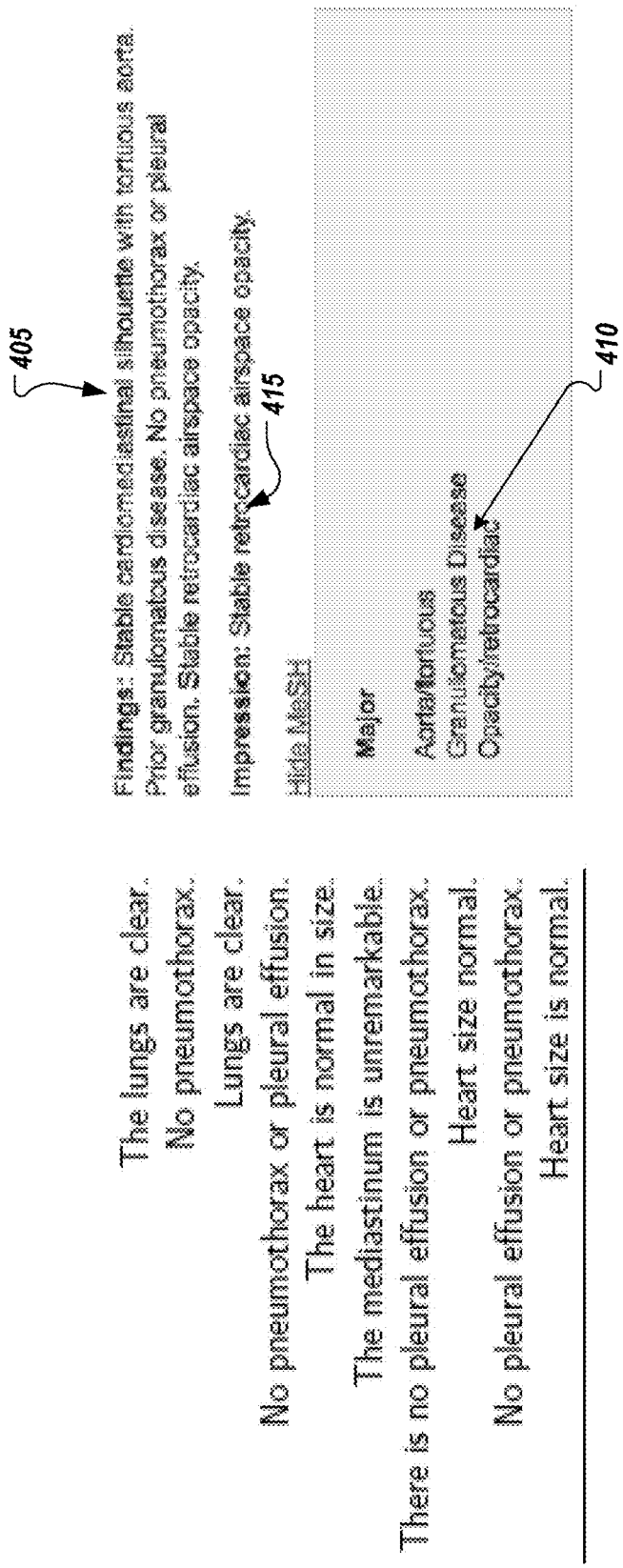
FIGS. 4(a) and 4(b) illustrates different approaches for automatically annotating abnormal sentences in accordance with example implementations of the present application.

Example implementations may use a variety of approaches to automate the abnormal sentence annotation model 225 illustrated in FIGS. 2 and 3. For example, a first approach may assume sentences relate to a medical abnormality when a sentence is detected as being differential sentences to a sentence describing a normal routine examination. FIG. 4(*a*) illustrates a group of normal routine examination comments which frequently appear in normal cases extracted from a public data set of chest x-ray image reports released by Indiana University. By detecting sentences in the training data which are differential from normal routine examination comments, sentences related to medical abnormalities may be detected. For example, abnormal sentence annotation model may be trained to calculating differential between normal routine examination comments (e.g., "lungs are clear", "no pneumothorax or pleural effusion", "the heart is normal in size", etc.) extracted from the public data set and similar sentences identified in the training data (e.g., "lungs are not clear", "pneumothorax identified", "pleural effusion identified", "the heart is enlarged in size").

By identifying common patterns in the "normal sentences", unclassified sentences in report may be compared to the "normal sentence" patterns and as signed a probability of being normal or abnormal based on the similarity to "normal sentence" patterns. The probabilities of being normal or abnormal may then be used to annotate the sentences of training data as normal or abnormal automatically.

As another example, a second approach to the automate abnormal sentence annotation model may assume sentences detected as being relevant to Medical Subject Headings (MeSH) terms (or some other type of predefined medical subjective terms) associated with the report are likely to occur regarding medical anomalies. Thus the second approach may determine relevance between a sentence in the text report of the training data and a MeSH term of a report by using the distance of the respective representations on a word vector space. FIG. 4(*b*) illustrates an example report tagged with MeSH terms that may be used as part of training data in an example implementation of the present application. As illustrated, the MeSH terms 410 have been extracted from the statement of findings 405 and the impression 415. The extracted MeSH terms 410 may be used to identify sentences of the findings 405 and impression 415 that have a higher probability of representing medical abnormalities.

By using the MeSH terms, a comparison may be made to known abnormal sentences and unclassified sentences may be classified as normal or abnormal based on the similarity.

Thus, in some example implementations, a content-based abnormal sentence classification model may be trained using human annotations or annotations obtained by one or more of the above described approaches. The abnormal sentence classification model can be then used to identifying abnormal sentences when no human annotations, reference normal routine examination or MeSH terms are available, e.g., a text report generated in the test phase.

In a third possible approach, a neural network may be trained with manually labeled training data and the trained neural network would automatically label sentences during the testing phase. For example, during the training phase, a given set of sentences may each be manually labeled (e.g., by a human operator) as either normal or abnormal. These manually labeled sentences may then be used to train a neural network to extract the text features and learn the association between the text features and the labels. Then, during the testing phase, the trained neural network may then automatically predict whether an input sentence is normal or abnormal.

Evaluation

Applicants conducted evaluation testing of example implementations in support of this application. A public dataset released by Indiana University was used for training models and evaluation. The dataset included 7,470 chest X-ray images and corresponding text reports. Each text report was labeled with a set of MeSH terms. Another public dataset, ChestX-ray14, released by the National Institutes of Health was used for learning image features. This dataset comprises 112,120 chest X-ray images. The training, verification and testing were partitioned into 90%, 5% and 5% of the dataset, respectively.

In the evaluated example implementation, the image feature learning was based on VGG-Net, a neural network based approach. The text generation was based on a Hierarchical LSTM and further integrated with sentence annotations that were calculated through the similarity between a sentence and a MeSH term of a text report on a word vector space. The word vector space was trained by the PubMed dataset that comprises 2.8 billion tokens in 22 million biomedical documents.

Figure 6:
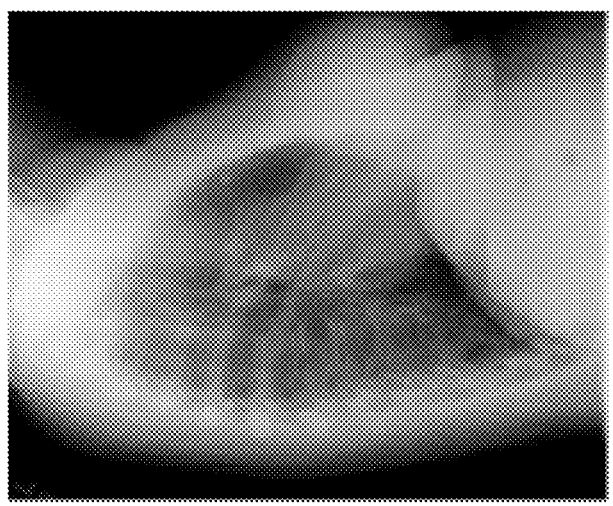

FIGS. 5 and 6 illustrate examples of a generated text reports for input X-ray images in accordance with example implementations of the present application[2]. In FIG. 5, a

[2]Medical image in FIG. 5 was obtained from NIH Clinical Center Repository available at https://openi.nlm.nih.gov/detailedresult?img=CXR1900_IM-0584-2001&query=stable%20appearance%20of%20the%20chest.%20no%acute%20process&it=xg&req=4Z&npos=2 and discussed in Wang X, Peng Y, Lu L, Lu Z, Bagheri M, Summers R M. report (b-510) generated by our approach can catch the medical abnormality (highlighted by box 520) while the report (a-505) generated by a baseline without considering abnormal sentence annotations only identifies normal routine examination comments and fails to describe abnormalities. For comparison, ground truth notes (c-515) dictated by a doctor are also illustrated in FIG. 5.

Another example of a generated text report is shown in FIG. 6 with a report (b-610) produced by an example implementation of the present application being illustrated in comparison to a baseline report (a-605), with the proposed model (b-610) being able to better catch the medical abnormality (highlighted by box 620) than the baseline model (a). For comparison, ground truth notes (c-615) dictated by a doctor are also illustrated in FIG. 6.

Example Computing Environment

Figure 7:
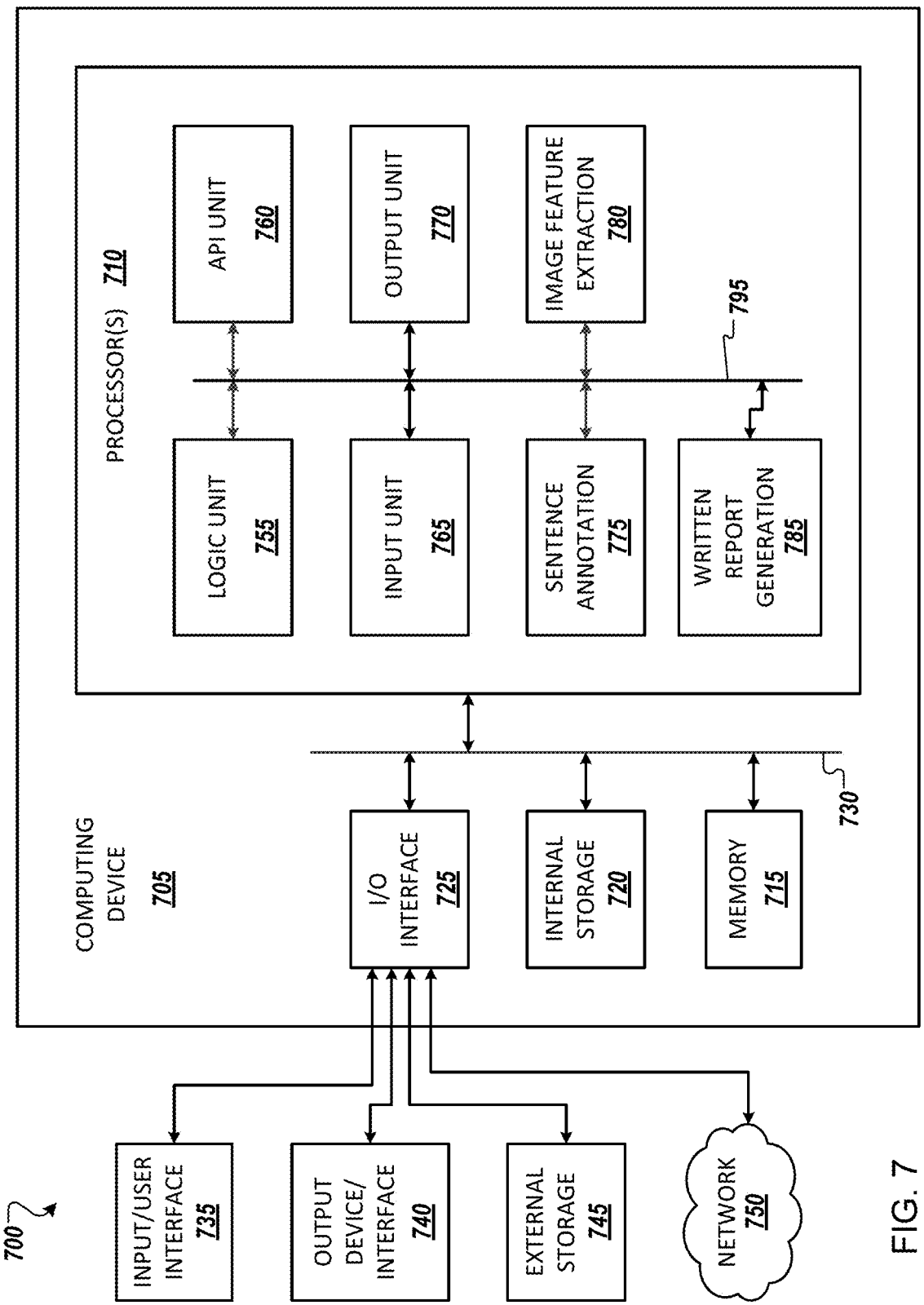
FIG. 7 illustrates an example computing environment with an example computer device suitable for use in some example implementations of the present application.

FIG. 7 illustrates an example computing environment 700 with an example computer device 705 suitable for use in some example implementations. Computing device 705 in computing environment 700 can include one or more processing units, cores, or processors 710, memory 715 (e.g., RAM, ROM, and/or the like), internal storage 720 (e.g., magnetic, ChestX-ray8: Hospital-scale Chest X-ray Database and Benchmarks on Weakly-Supervised Classification and Localization of Common Thorax Diseases. IEEE CVPR 2017, http://openaccess.thecvf.com/content_cvpr_2017/papers/Wang_ChestX-ray8_Hospital-Scale_Chest_CVPR_2017_paper.pdf Medical image in FIG. 6 were obtained from NIH Clinical Center Repository available at https://openi.nlm.nih.gov/detailedresult?img=CXR1246_IM-0167-2001&query=No%20acute%20findings.%20Cardiac%20mediastinal%20contours%20are%20within%20normal%20limits.%20Prior%20granulomatous&it=xg&req=4&npos=10 and discussed in Wang X, Peng Y, Lu L, Lu Z, Bagheri M, Summers R M. ChestX-ray8: Hospital-scale Chest X-ray Database and Benchmarks on Weakly-Supervised Classification and Localization of Common Thorax Diseases. IEEE CVPR 2017, http://openaccess.thecvf.com/content_cvpr_2017/papers/Wang_ChestX-ray8_Hospital-Scale_Chest_CVPR_2017_paper.pdf optical, solid state storage, and/or organic), and/or I/O interface 725, any of which can be coupled on a communication mechanism or bus 730 for communicating information or embedded in the computing device 705.

Computing device 705 can be communicatively coupled to input/interface 735 and output device/interface 740. Either one or both of input/interface 735 and output device/interface 740 can be a wired or wireless interface and can be detachable. Input/interface 735 may include any device, component, sensor, or interface, physical or virtual, which can be used to provide input (e.g., buttons, touch-screen interface, keyboard, a pointing/cursor control, microphone, camera, braille, motion sensor, optical reader, and/or the like).

Output device/interface 740 may include a display, television, monitor, printer, speaker, braille, or the like. In some example implementations, input/interface 735 (e.g., user interface) and output device/interface 740 can be embedded with, or physically coupled to, the computing device 705. In other example implementations, other computing devices may function as, or provide the functions of, an input/interface 735 and output device/interface 740 for a computing device 705. These elements may include, but are not limited to, well-known AR hardware inputs so as to permit a user to interact with an AR environment.

Examples of computing device 705 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, server devices, other computers, information kiosks, televisions with one or more processors embedded therein and/or coupled thereto, radios, and the like).

Computing device 705 can be communicatively coupled (e.g., via I/O interface 725) to external storage 745 and network 750 for communicating with any number of networked components, devices, and systems, including one or more computing devices of the same or different configuration. Computing device 705 or any connected computing device can be functioning as, providing services of, or referred to as a server, client, thin server, general machine, special-purpose machine, or another label.

I/O interface 725 can include, but is not limited to, wired and/or wireless interfaces using any communication or I/O protocols or standards (e.g., Ethernet, 702.11xs, Universal System Bus, WiMAX, modem, a cellular network protocol, and the like) for communicating information to and/or from at least all the connected components, devices, and network in computing environment 700. Network 750 can be any network or combination of networks (e.g., the Internet, local area network, wide area network, a telephonic network, a cellular network, satellite network, and the like).

Computing device 705 can use and/or communicate using computer-usable or computer-readable media, including transitory media and non-transitory media. Transitory media includes transmission media (e.g., metal cables, fiber optics), signals, carrier waves, and the like. Non-transitory media includes magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computing device 705 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Processor(s) 710 can execute under any operating system (OS) (not shown), in a native or virtual environment. One or more applications can be deployed that include logic unit 755, application programming interface (API) unit 760, input unit 765, output unit 770, sentence annotation unit 775, image feature extraction unit 780, written report generation unit 785 and inter-unit communication mechanism 795 for the different units to communicate with each other, with the OS, and with other applications (not shown).

For example, sentence annotation unit 775, image feature extraction unit 780, and written report generation unit 785 may implement one or more processes shown in FIGS. 2 and 3. The described units and elements can be varied in design, function, configuration, or implementation and are not limited to the descriptions provided.

In some example implementations, when information or an execution instruction is received by API unit 760, it may be communicated to one or more other units (e.g., sentence annotation unit 775, image feature extraction unit 780, and written report generation unit 785). For example, sentence annotation unit 775 may automatically annotate sentences of a written report that are determined to be indicative of abnormalities and provide the annotations to the written report generation unit 785. Further, image feature extraction unit 780 may extract image features from one or more image files associated with the written reports and provide the extracted image features to the written report generation unit 785. Further, the written report generation unit 785 may generate one or more written reports based on the annotations provided by the sentence annotation unit 775 and the extracted image features provided by the image feature extraction unit 780. The written report generation unit 785 may be exported via the output unit 770.

In some instances, the logic unit 755 may be configured to control the information flow among the units and direct the services provided by API unit 760, input unit 765, sentence annotation unit 775, image feature extraction unit 780, and written report generation unit 785 in some example implementations described above. For example, the flow of one or more processes or implementations may be controlled by logic unit 755 alone or in conjunction with API unit 760.

Although a few example implementations have been shown and described, these example implementations are provided to convey the subject matter described herein to people who are familiar with this field. It should be understood that the subject matter described herein may be implemented in various forms without being limited to the described example implementations. The subject matter described herein can be practiced without those specifically defined or described matters or with other or different elements or matters not described. It will be appreciated by those familiar with this field that changes may be made in these example implementations without departing from the subject matter described herein as defined in the appended claims and their equivalents.

What is claimed is:

1. A method of determining a treatment order to review medical images and treat patients from a plurality of patient imaging records, the method comprising:
    executing a testing process that comprises:
        extracting, by a neural network, second image features from each of the plurality of patient imaging records;
        inputting, by the neural network, the second image features from each of the plurality of patient imaging records into an imaging report generation model;
        generating, by the neural network, a written report associated with each of the plurality of patient imaging records based on the second image features inputted into the imaging report generation model, the imaging report generation model trained prior to the testing process based on a plurality of training imaging records associated with predetermined text reports, wherein each generated written report comprises a plurality of written sentences;
        annotating, by the neural network, as medically abnormal one or more written sentences of the generated written reports based on a sentence annotation model that provides abnormality annotations on an individual sentence basis;
        determining, by the neural network, an abnormality score associated with each written report, each abnormality score representing a number of written sentences identified as indicative of a medial abnormality in each written report; and
        providing the generated written reports to a treating physician in a sorted order based on the abnormality score associated with each written report.

2. The method of claim 1, wherein, prior to executing the testing process, the neural network is trained by a training process using the plurality of training imaging records each associated with a predetermined text report, the training process comprising:
    analyzing, by the neural network, each predetermined text report based on the sentence annotation model to generate sentence-wise abnormality annotations associated with predetermined individual sentences of the predetermined text report;
    extracting, by the neural network, first image features from each of the training imaging records; and
    inputting, by the neural network, the first image features from each of the plurality of training imaging records and the predetermined text report having sentence-wise abnormality annotations into the imaging report generation model;

training, by the neural network, the imaging report generation model by associating the first image features with the predetermined text report having sentence-wise abnormality annotations.

3. The method of claim 2, wherein the sentence annotation model automatically annotates abnormal sentences by:

collecting a plurality of predetermined text reports indicative of normal imaging features;

extracting normal sentence patterns from the plurality of predetermined text reports indicative of normal imaging features;

comparing each sentence in a generated written report to be annotated to the extracted normal sentence patterns; and annotating as abnormal each sentence in the generated written report for which the comparing to the extracted normal sentence patterns indicates a similarity below a threshold.

4. The method of claim 2, wherein the sentence annotation model automatically annotates abnormal sentences by:

during the training process, training the neural network to develop an association between text features and label data indicative of an abnormal sentence using a plurality of training sentences, each of the plurality of training sentences being previously labeled as either normal or abnormal; and during the testing process, using the neural network to determine whether a subject written sentence is either normal or abnormal.

5. The method of claim 1, wherein the generating the written report associated with each of the plurality of patient imaging records further comprises:

determining a plurality of topics for the written report based on the second image features extracted by the neural network;

generating a written sentence associated with each of the plurality of determined topics; and combining the generated written sentences to produce the written report.

6. The method of claim 5, wherein the generating the written sentence associated with each of the plurality of determined topics comprises:

determining a first word in the sentence based on the imaging report generation model, the determined topic associated with the sentence, and the second image feature associated with the determined topic; and sequentially determining a plurality of subsequent words in the sentence based on (a) the imaging report generation model, (b) the determined topic associated with the sentence, (c) the second image feature associated with the determined topic, and (d) one or more of (i) the determined first word in the sentence and (ii) a previously determined word from the plurality of subsequent words.

7. The method of claim 1, wherein the generating each written sentence in the written report associated with each of the plurality of patient imaging records further comprises determining a sentence confidence score based on a likelihood probability associated with each word in the generated written sentence; and generating the written report further comprises generating a written report confidence score based on the determined sentence confidence score associated with each written sentence in the written report.

8. The method of claim 1, wherein the sentence annotation model automatically annotates abnormal sentences by:

for each written sentence in a generated written report to be annotated, determining the semantic similarity between one of a plurality of pre-defined medical subject terms and the written sentence, the pre-defined medical subject terms indicative of a medical abnormality; and annotating as abnormal, any sentence in the generated written report that is determined to be semantically similar to one or more of the plurality of pre-defined medical subject terms.

9. A non-transitory computer readable medium encoded with instructions for making a computing device execute a method of determining a treatment order to review medical images and treat patients from a plurality of patient imaging records the method comprising:

executing a testing process that comprises:

extracting, by a neural network, second image features from each of the plurality of patient imaging records;

inputting, by the neural network, the second image features from each of the plurality of patient imaging records into an imaging report generation model;

generating, by the neural network, a written report associated with each of the plurality of patient imaging records based on the second image features inputted into the imaging report generation model, the imaging report generation model trained prior to the testing process based on a plurality of training imaging records associated with predetermined text reports, wherein each generated written report comprises a plurality of written sentences;

annotating, by the neural network, as medically abnormal one or more written sentences of the generated written reports based on a sentence annotation model that provides abnormality annotations on an individual sentence basis;

determining, by the neural network, an abnormality score associated with each written report, each abnormality score representing a number of written sentences identified as indicative of a medial abnormality in each written report; and providing the generated written reports to a treating physician in a sorted order based on the abnormality score associated with each written report.

10. The non-transitory computer readable medium of claim 9, wherein, prior to executing the testing process, the neural network is trained by the training process using a plurality of training imaging records each associated with a predetermined text report, the training process comprising:

analyzing, by the neural network, each predetermined text report based on the sentence annotation model to generate sentence-wise abnormality annotations associated with predetermined individual sentences of the predetermined text report;

extracting, by the neural network, first image features from each of the training imaging records; and inputting, by the neural network, the first image features from each of the plurality of training imaging records and the predetermined text report having sentence-wise abnormality annotations into the imaging report generation model;

training, by the neural network, the imaging report generation model by associating the first image features with the predetermined text report having sentence-wise abnormality annotations.

11. The non-transitory computer readable medium of claim 10, wherein the sentence annotation model automatically annotates abnormal sentences by:
  collecting a plurality of predetermined text reports indicative of normal imaging features;
  extracting normal sentence patterns from the plurality of predetermined text reports indicative of normal imaging features;
  comparing each sentence in a generated written report to be annotated to the extracted normal sentence patterns; and
  annotating as abnormal each sentence in the generated written report for which the comparing to the extracted normal sentence patterns indicates a similarity below a threshold.

12. The non-transitory computer readable medium of claim 9, w wherein the generating the written report associated with each of the plurality of patient imaging records further comprises:
  determining a plurality of topics for the written report based on the second image features extracted by the neural network;
  generating a written sentence associated with each of the plurality of determined topics; and
  combining the generated written sentences to produce the written report.

13. The non-transitory computer readable medium of claim 12, wherein the generating the written sentence associated with each of the plurality of determined topics comprises:
  determining a first word in the sentence based on the imaging report generation model, the determined topic associated with the sentence, and the second image feature associated with the determined topic; and
  sequentially determining a plurality of subsequent words in the sentence based on (a) the imaging report generation model, (b) the determined topic associated with the sentence, (c) the second image feature associated with the determined topic, and (d) one or more of (i) the determined first word in the sentence and (ii) a previously determined word from the plurality of subsequent words.

14. The non-transitory computer readable medium of claim 9, wherein the generating each written sentence in the written report associated with each of the plurality of patient imaging records further comprises determining a sentence confidence score based on a likelihood probability associated with each word in the generated written sentence; and
  generating the written report further comprises generating a written report confidence score based on the determined sentence confidence score associated with each written sentence in the written report.

15. The non-transitory computer readable medium of claim 9, wherein the sentence annotation model automatically annotates abnormal sentences by:
  for each written sentence in a generated written report to be annotated, determining the semantic similarity between one of a plurality of pre-defined medical subject terms and the written sentence, the pre-defined medical subject terms indicative of a medical abnormality; and
  annotating as abnormal, any sentence in the generated written report that is determined to be semantically similar to one or more of the plurality of pre-defined medical subject terms.

16. A computing device comprising:
  a memory storage device storing a plurality of patient imaging records; and
  a processor communicatively coupled to the memory storage device, the processor configured to perform a method of determining a treatment order to review medical images and treat patients from a plurality of patient imaging records, the method comprising:
    executing a testing process that comprises:
      extracting, by a neural network, second image features from each of the plurality of patient imaging records;
      inputting, by the neural network, the second image features from each of the plurality of patient imaging records into an imaging report generation model;
      generating, by the neural network, a written report associated with each of the plurality of patient imaging records based on the second image features inputted into the imaging report generation model, the imaging report generation model trained prior to the testing process based on a plurality of training imaging records associated with predetermined text reports, wherein each generated written report comprises a plurality of written sentences;
      annotating, by the neural network, as medically abnormal one or more written sentences of the generated written reports based on a sentence annotation model that provides abnormality annotations on an individual sentence basis;
      determining, by the neural network, an abnormality score associated with each written report, each abnormality score representing a number of written sentences identified as indicative of a medial abnormality in each written report; and
      providing the generated written reports to a treating physician in a sorted order based on the abnormality score associated with each written report.

17. The computing device of claim 16, wherein, prior to executing the testing process, the neural network is trained by a training process using the plurality of training imaging records each associated with a predetermined text report, the training process comprising:
  analyzing, by the neural network, each predetermined text report based on the sentence annotation model to generate sentence-wise abnormality annotations associated with predetermined individual sentences of the predetermined text report;
  extracting, by the neural network, first image features from each of the training imaging records; and
  inputting, by the neural network, the first image features from each of the plurality of training imaging records and the predetermined text report having sentence-wise abnormality annotations into the imaging report generation model;
  training, by the neural network, the imaging report generation model by associating the first image features with the predetermined text report having sentence-wise abnormality annotations.

18. The computing device of claim 17, wherein the sentence annotation model automatically annotates abnormal sentences by:
  collecting a plurality of predetermined text reports indicative of normal imaging features;

extracting normal sentence patterns from the plurality of predetermined text reports indicative of normal imaging features;

comparing each sentence in a generated written report to be annotated to the extracted normal sentence patterns; and annotating as abnormal each sentence in the generated written report for which the comparing to the extracted normal sentence patterns indicates a similarity below a threshold.

19. The computing device of claim 16, wherein the generating the written report associated with each of the plurality of patient imaging records further comprises:

determining a plurality of topics for the written report based on the second image features extracted by the neural network;

generating a written sentence associated with each of the plurality of determined topics; and combining the generated written sentences to produce the written report, wherein the generating the written sentence associated with each of the plurality of determined topics comprises:

determining a first word in the sentence based on the imaging report generation model, the determined topic associated with the sentence, and the second image feature associated with the determined topic; and sequentially determining a plurality of subsequent words in the sentence based on (a) the imaging report generation model, (b) the determined topic associated with the sentence, (c) the second image feature associated with the determined topic, and (d) one or more of (i) the determined first word in the sentence and (ii) a previously determined word from the plurality of subsequent words.

20. The computing device of claim 16, wherein the sentence annotation model automatically annotates abnormal sentences by:

for each written sentence in a generated written report to be annotated, determining the semantic similarity between one of a plurality of pre-defined medical subject terms and the written sentence, the pre-defined medical subject terms indicative of a medical abnormality; and annotating as abnormal, any sentence in the generated written report that is determined to be semantically similar to one or more of the plurality of pre-defined medical subject terms.

* * * * *